(12) United States Patent
Fleischmann

(10) Patent No.: US 9,055,780 B2
(45) Date of Patent: *Jun. 16, 2015

(54) KNEE IMPLANTS HAVING HYDROMAGNETIC JOINTS

(71) Applicant: ROAR Labs, LLC, Middleton, WI (US)

(72) Inventor: David T. Fleischmann, Madison, WI (US)

(*) Notice: Subject to any disclaimer, the term of this patent is extended or adjusted under 35 U.S.C. 154(b) by 107 days.

This patent is subject to a terminal disclaimer.

(21) Appl. No.: 13/903,170

(22) Filed: May 28, 2013

(65) Prior Publication Data

US 2013/0261756 A1    Oct. 3, 2013

Related U.S. Application Data

(63) Continuation of application No. 13/046,949, filed on Mar. 14, 2011, now Pat. No. 8,449,615, which is a continuation-in-part of application No. 13/031,566, filed on Feb. 21, 2011, now Pat. No. 8,454,692.

(60) Provisional application No. 61/325,357, filed on Apr. 18, 2010.

(51) Int. Cl.
| | |
|---|---|
| *A61F 2/38* | (2006.01) |
| *A43B 7/32* | (2006.01) |
| *A61F 2/44* | (2006.01) |

(Continued)

(52) U.S. Cl.
CPC ... *A43B 7/32* (2013.01); *A61F 2/38* (2013.01); *A61F 2/442* (2013.01); *A61F 2002/30079* (2013.01); *A61F 2002/30563* (2013.01); *A61F 2002/30581* (2013.01); *A61F 2002/30677* (2013.01); *A61F 2002/30841* (2013.01); *A61F 2002/4698* (2013.01); *A61F 2210/009* (2013.01); *A61F 2/3836* (2013.01)

(58) Field of Classification Search
CPC ......... A61F 2/38; A61F 2/442; A61F 2/3836; A61F 2002/30079; A61F 2002/30563; A61F 2002/30581; A61F 2002/30841; A61F 2002/4698; A61F 2002/30677; A61F 2210/009; A43B 7/32
USPC .......... 623/20.28–20.35, 17.11–17.16, 11.11, 623/16.11, 18.12; 403/40
See application file for complete search history.

(56) References Cited

U.S. PATENT DOCUMENTS

| | | |
|---|---|---|
| 4,904,260 A | 2/1990 | Ray et al. |
| 5,192,326 A | 3/1993 | Bao et al. |
| 5,674,295 A | 10/1997 | Ray et al. |

(Continued)

*Primary Examiner* — Pedro Philogene
(74) *Attorney, Agent, or Firm* — Doherty IP Law Group LLC

(57) ABSTRACT

A knee implant includes a first implant part adapted for attachment to a femur and a second implant part adapted for attachment to a tibia. The knee implant includes a hydromagnetic joint having a first magnetic element with a first magnetically charged surface and a first buoyant element coupled with the first magnetic element, and a second magnetically charged surface that opposes the first magnetically charged surface of the first magnetic element and a second buoyant element coupled with the second magnetic element. A fluid body is disposed between the first and second buoyant elements, and the first and second buoyant elements are in fluid communication with one another through the fluid body. The hydromagnetic joint has an enclosure extending between the first and second buoyant elements for containing the fluid body therebetween, whereby the first and second buoyant elements are moveable relative to one another.

20 Claims, 14 Drawing Sheets

(51) Int. Cl.
*A61F 2/30* (2006.01)
*A61F 2/46* (2006.01)

(56) References Cited

U.S. PATENT DOCUMENTS

| | | | |
|---|---|---|---|
| 5,824,093 A | 10/1998 | Ray et al. | |
| 6,022,376 A | 2/2000 | Assell et al. | |
| 6,984,246 B2 * | 1/2006 | Huang | 623/17.13 |
| 7,381,223 B2 * | 6/2008 | Kovacevic | 623/20.32 |
| 7,731,753 B2 * | 6/2010 | Reo et al. | 623/17.13 |
| 7,811,328 B2 * | 10/2010 | Molz et al. | 623/17.16 |
| 8,026,729 B2 * | 9/2011 | Kroh et al. | 324/633 |
| 8,043,290 B2 * | 10/2011 | Harrison et al. | 606/60 |
| 8,114,158 B2 | 2/2012 | Carl et al. | |
| 8,128,699 B2 | 3/2012 | Justis et al. | |
| 8,454,692 B2 * | 6/2013 | Fleischmann | 623/16.11 |
| 2002/0032484 A1 | 3/2002 | Hyde, Jr. | |
| 2003/0187510 A1 | 10/2003 | Hyde | |
| 2004/0133281 A1 | 7/2004 | Khandkar et al. | |
| 2006/0247782 A1 | 11/2006 | Molz, IV et al. | |
| 2007/0233254 A1 | 10/2007 | Grotz et al. | |
| 2011/0257749 A1 | 10/2011 | Fleischmann | |
| 2011/0257754 A1 | 10/2011 | Fleischmann | |
| 2012/0109197 A1 | 5/2012 | Carl et al. | |

* cited by examiner

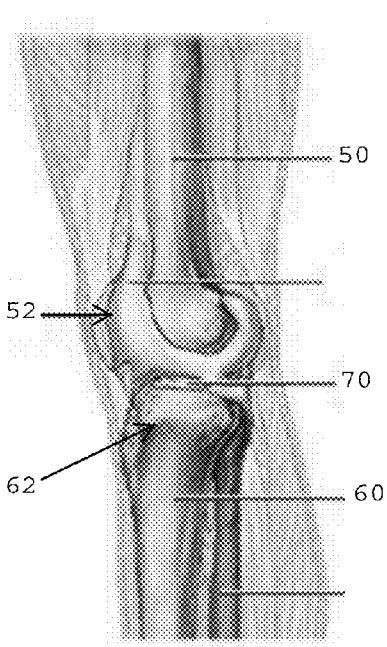 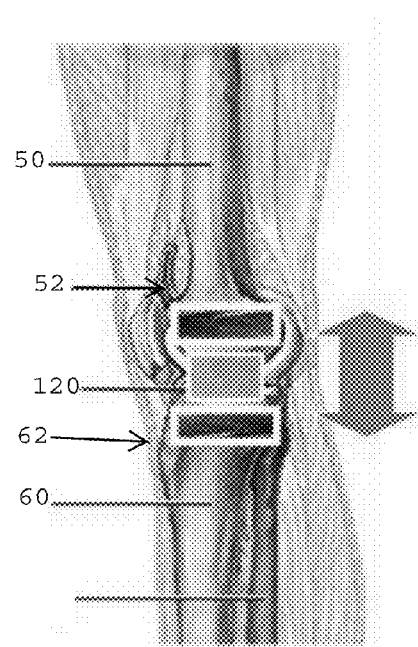
FIG. 3A　　　　　　　　　　FIG. 3B
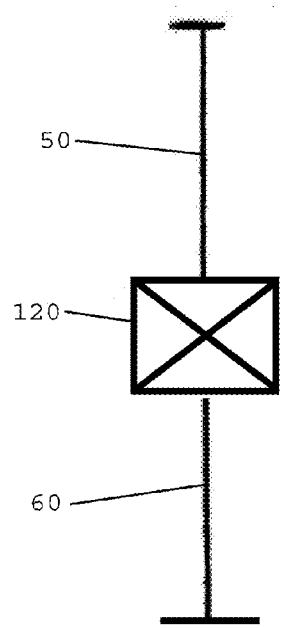
FIG. 4

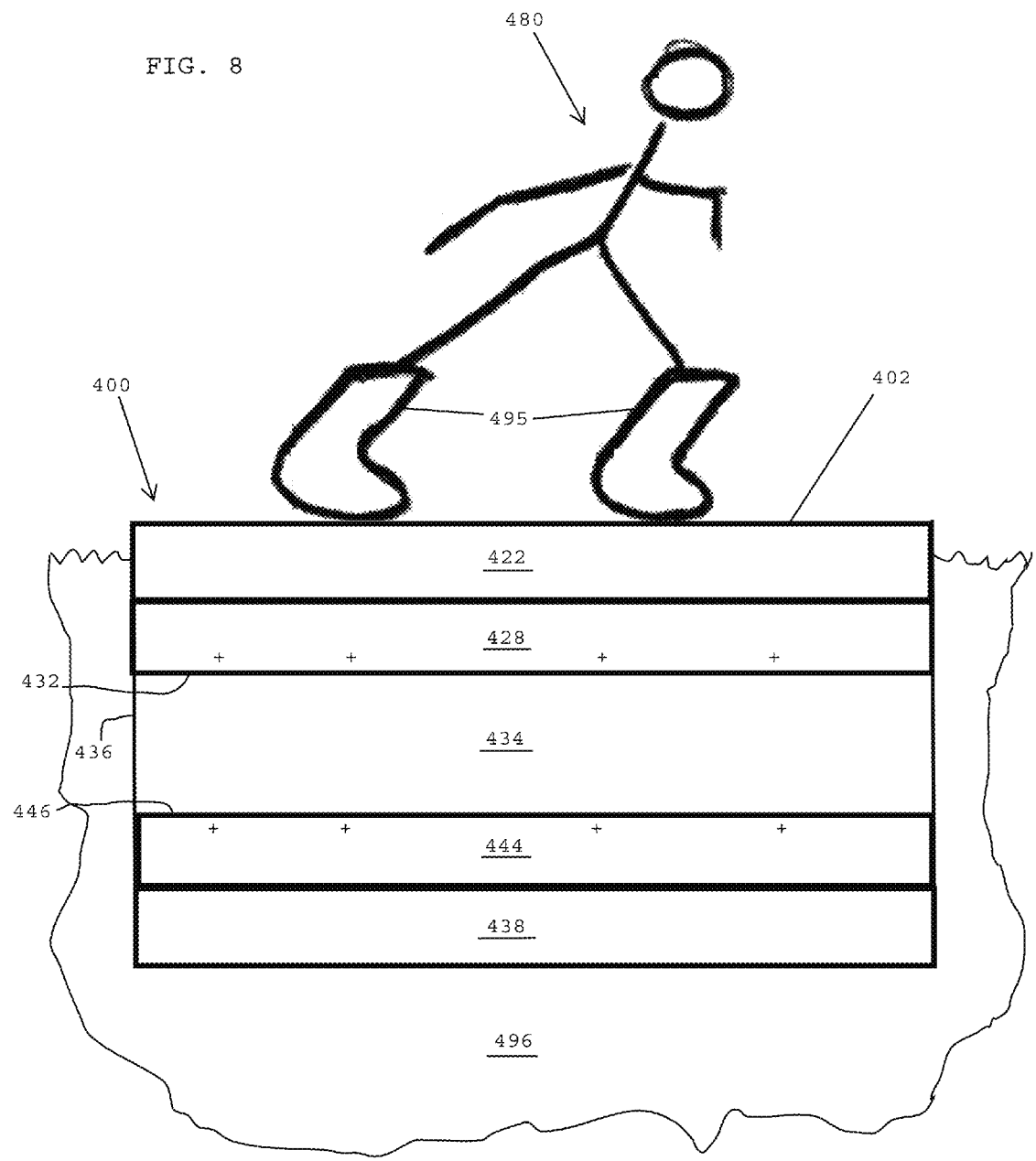

FIG. 12A
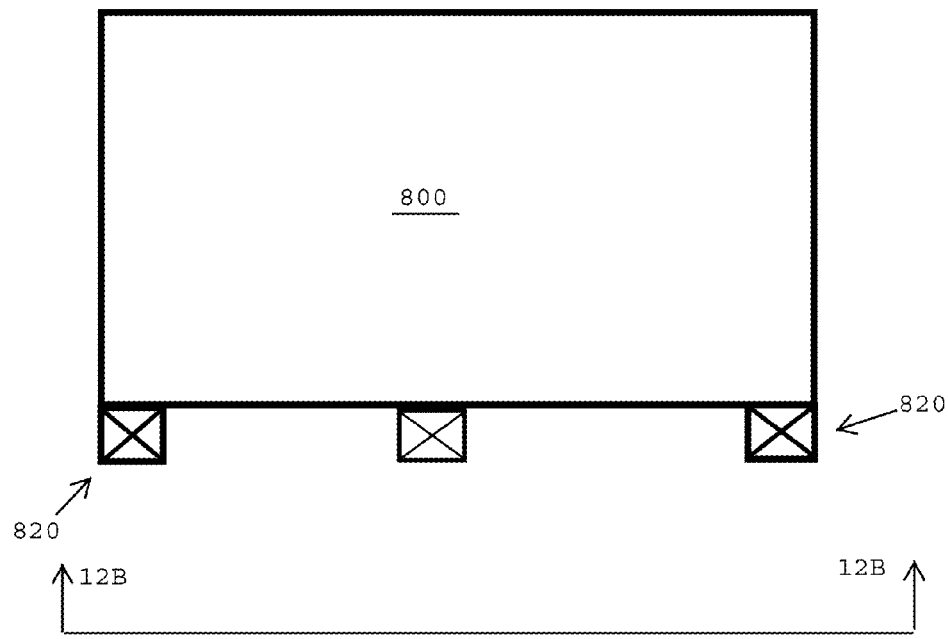
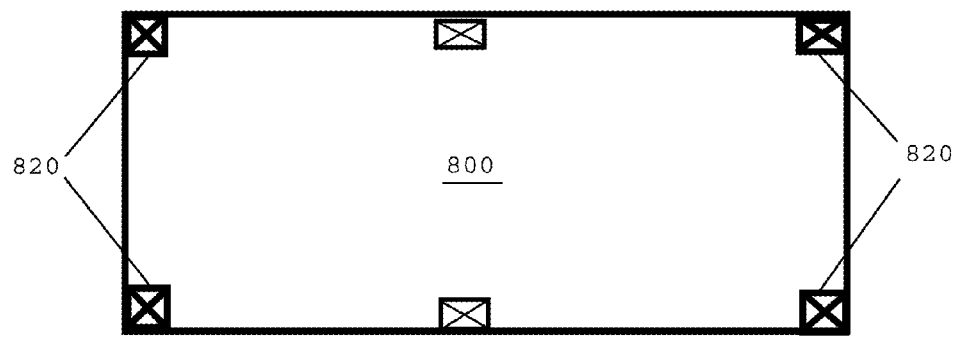
FIG. 12B

KNEE IMPLANTS HAVING HYDROMAGNETIC JOINTS

CROSS REFERENCE TO RELATED APPLICATIONS

The present application is a continuation of U.S. patent application Ser. No. 13/046,949, filed Mar. 14, 2011, issued on even date herewith as U.S. Pat. No. 8,449,615, which is a continuation-in-part of U.S. patent application Ser. No. 13/031,566, filed Feb. 21, 2011, now allowed, which, in turn, claims benefit of U.S. Provisional Application Ser. No. 61/325,357, filed Apr. 18, 2010, the disclosures of which are hereby incorporated by reference herein.

BACKGROUND OF THE INVENTION

1. Field of the Invention

The present invention relates to joints and springs, and more specifically relates to moveable joints and springs for mechanical systems and medical devices such as intervertebral implants and knee implants.

2. Description of the Related Art

A joint is a structure that joins together two separate parts. Some joints unite the two parts rigidly, however, other joints permit motion between the two parts. Some joints are reinforced with nails, screws, or glue, such as a joint forming a connection between two pieces of wood or metal.

In a human body, a joint is the moveable or fixed place where two bones or elements of a skeleton are joined together. Recently, moveable artificial joints have been incorporated into medical implant devices such as artificial knees, artificial hips, and spinal implants such as intervertebral discs. By 2012, the joint reconstruction market is expected to grow from $12.2 to $17.4 billion. By 2016, the spinal implant market is expected to grow from $6.5 to $10.3 billion.

Metal rods and pedicle screws are often used during spinal fusion procedures. Physiological drawbacks of using metal rods for spinal fusion include decreased motion, pain, degeneration of joints, stiffness, epidural searing and muscle stripping. Other drawbacks include the high costs associated with physical therapy and rehabilitation, and instances of post-surgical infection.

One problem with joints for mechanical systems and medical devices is that they tend to wear out and must be replaced. Other problems include gel extrusion, joint/surface friction and bone resorption. Another problem is that joints do not sufficiently dampen vibrational, compression and tension forces, resulting in energy losses and the generation of excessive noise. In addition, moveable artificial joints do not accurately replicate the natural movement of the human body.

In view of the above problems, there remains a need for improved joints for mechanical systems and medical devices that are durable, conserve energy, sufficiently absorb vibrational, compression and tension forces, and minimize noise. Moreover, there is a need for hydromagnetic joints that increase physiological effectiveness by increasing motion, and decrease friction and pain, and that decrease research and development and material costs, and increase durability.

SUMMARY OF THE INVENTION

In one embodiment, a hydromagnetic joint preferably includes a first joint part including a first magnetic element having a magnetically charged surface, and a first buoyant element coupled with the first magnetic element, and a second joint part including a second magnetic element having a second magnetically charged surface that opposes the first magnetically charged surface of the first magnetic element, and a second buoyant element coupled with the second magnetic element. The joint desirably includes a liquid, such as water or saline solution, disposed between the first and second joint parts, whereby the first and second joint parts are moveable relative to one another and are in fluid communication with the liquid.

In one embodiment, the liquid is contained within an enclosure that is disposed between the first and second joint parts. In one embodiment, the enclosure for the liquid is flexible so that the shape of the liquid body may change in response to external forces such as compression, tension and vibrational forces transferred from the first and second joint parts.

In one embodiment, as least one of the first and second joint parts preferably includes a solid body having at least one aperture extending therethrough that is adapted for enabling the liquid to pass through the at least one aperture. The at least one aperture may include a plurality of apertures. The size and number of apertures may be modified for controlling the compression rate of the hydromagnetic joint. For example, if it is desirable to provide for more rapid compression of a hydromagnetic joint, more apertures may be provided through the body of one of the first and second joint parts. The size or diameter of the apertures may also be modified for controlling the compression rate. On the other hand, if it is desirable to slow down the compression rate, fewer apertures or apertures having a smaller diameter may be provided.

In one embodiment, the first and second joint parts are moveable relative to one another. In one embodiment, the first and second joint parts are preferably aligned with one another along an axis and are moveable relative to one another along the axis.

In one embodiment, the magnetic elements comprise magnetic materials including ferromagnetic, diamagnetic, and electromagnetic materials, or any other well-known magnetic materials.

In one embodiment, in response to compression forces, the first and second joint parts are adapted to move toward one another for compressing the liquid therebetween. The first and second magnetically charged surfaces desirably have the same polarity and are adapted to repel one another when the first and second parts are compressed toward one another.

In one embodiment, as the first and second joint parts are compressed toward one another, the first and second joint parts transfer the compressing force to the liquid. The flexible enclosure or flexible diaphragm containing the liquid enables the shape of the liquid body to change in response to the compression forces. The resistance provided by the liquid body dampens the compression rate for the first and second joint parts. In addition, the first and second magnetically charged surfaces having the same polarity will repel one another when the first and second parts move toward one another. The repelling force will increase as the first and second magnetically charged surfaces move closer to one another. Thus, the compression rate of the hydromagnetic joint is dampened by both the resistance provided by the liquid body and the repelling magnetic force between the first and second joint parts.

In one embodiment, the hydromagnetic joint may be incorporated into a medical implant device such as a knee replacement implant, a hip replacement implant, a bone implant, and/or a spinal implant such as an intervertebral device or a device that replaces one or more vertebrae. In one embodiment, a medical device having an electromagnetic joint may be used to replace multiple vertebrae. In one embodiment, an intervertebral device has a near frictionless joint that preserves both vertebral segment mobility as well as resisting axial compression. The hydromagnetic joint desirably allows for gradual resistance to axial compression that may not be achieved when using current disc replacement implants. Additionally, wear is nearly absent in the device having a hydromagnetic joint because there is nearly no metal to metal contact and no risk of UHMW polyethylene wear. In addition, the hydromagnetic surface distributes force across the entire joint endplate to prevent bone resorption, and gel extrusion seen in conventional devices cannot occur with the device disclosed in the present application. Finally, competing implants are prone to fragmentation with shearing loads, which is obviated with a spinal implant having a hydromagnetic joint.

In one embodiment, the hydromagnetic joint may also be incorporated into mechanical systems having moveable joints, such as car joints, power generation systems (e.g., generators), shoes and sneakers, and balance boards used for medical therapy.

It may be desirable to secure the hydromagnetic joint in place within a mechanical system or a patient's body. For example, a bore may be formed in bone and the anchoring element may be inserted into the bone for holding the hydromagnetic joint to the bone. The anchoring element disposed within the bone may include a hydromagnetic joint for dampening compression, tension, and vibrational forces. In one embodiment, a hydromagnetic joint preferably includes a first anchoring element coupled with the first joint part for anchoring the first joint part to a first object, and a second anchoring element coupled with the second joint part for anchoring the second joint part to a second object. In one embodiment, a hydromagnetic joint may be incorporated into an anchoring element.

In one embodiment, a medical implant preferably includes a first part including a first magnetic element having a magnetically charged surface and a first buoyant element coupled with the first magnetic element, a second part including a second magnetic element having a second magnetically charged surface that opposes the first magnetically charged surface of the first magnetic element and a second buoyant element coupled with the second magnetic element, and a liquid body disposed between the first and second parts, whereby the first and second parts are in fluid communication with the liquid body and are adapted to move relative to one another.

The first and second magnetically charged surfaces desirably have a common polarity so that the first and second magnetically charged surfaces repel one another. The medical implant preferably includes a first anchoring element coupled with the first part of the implant for attaching the first part to a first bone, and a second anchoring element coupled with the second part of the implant for attaching the second part to a second bone. In one embodiment, the first and second parts of the implant move relative to one another. In one embodiment, one of the first and second implant parts may remain stationary and the other one of the first and second implant parts is moveable relative to the other implant part. In one embodiment, the stationary implant part includes a relatively rigid or stationary reservoir for holding the liquid and the other implant part moves in a fashion similar to a piston within the reservoir. In one embodiment, the moveable implant part includes one or more apertures extending therethrough for enabling the liquid to pass through the apertures as the implant parts move toward one another. The size and/or the number of apertures provided will control the compression rate of the hydromagnetic joint. As noted above, the number of apertures and the size of the apertures may be modified to change the compression rate. The hydromagnetic joint may have shutters for modifying the size and/or the number of the apertures to change the compression rate of the joint, which may occur after the joint has been installed or implanted. In one embodiment, the shutters may be opened and closed and adjusted by a control system such as an electronic control system.

In one embodiment, an enclosure desirably extends between the first and second parts for containing the liquid body. The enclosure may be flexible for changing shape as the first and second parts move relative to one another.

In one embodiment, a balance board for providing balancing therapy desirably includes a first part having a first buoyant element, and a first magnetic element attached to the first buoyant element, the first magnetic element having a first magnetically charged surface, and a second part including a second buoyant element, and a second magnetic element attached to the second buoyant element, the second magnetic element having a second magnetically charged surface that opposes and repels the first magnetically charged surface. The balance board preferably includes a liquid body contained between the first and second parts with the first and second parts being in fluid communication with the liquid body and being adapted to move relative to one another.

In one embodiment, the balance board is used for rehabilitation and is particularly used for rehabilitating military personnel having amputated limbs. Placing the above-described balance board with a hydromagnetic joint in an external body of water has been shown to enhance balancing therapy for the above-described military personnel. In one embodiment, the balance board is held below the surface of the external body of water using restraining straps. The restraining straps perform a number of functions including holding the balance board below the top surface of the external body of water and limiting vertical and horizontal movement of the balance board within the external body of water.

In one embodiment, an intervertebral implant preferably includes a first part attached to a first vertebrae, the first part including a first magnetic element having a first magnetically charged surface and a first buoyant element coupled with the first magnetic element, and a second part attached to a second vertebrae, the second part including a second magnetic element having a second magnetically charged surface that opposes the first magnetically charged surface of the first magnetic element and a second buoyant element coupled with the second magnetic element. The implant desirably includes a fluid body, such as a liquid or gel, disposed between the first and second parts, whereby the first and second parts are in fluid communication with one another through the fluid body. An enclosure, such as a flexible enclosure, preferably extends between the first and second parts for containing the fluid body therebetween, whereby the first and second parts are preferably moveable relative to one another.

In one embodiment, the intervertebral implant desirably includes a first anchoring element coupled with the first part of the implant for attaching the first part to the first vertebrae, and a second anchoring element coupled with the second part of the implant for attaching the second part to the second vertebrae.

In one embodiment, the first and second magnetically charged surfaces oppose one another and have a common polarity so that the first and second magnetically charged surfaces repel one another. The repelling forces may be useful for dampening compression forces exerted upon the first and second implant parts.

In one embodiment, the flexible enclosure is adapted to change shape as the first and second parts move relative to one another. The fluid body and the flexible enclosure are adapted to change shape in response to compression forces exerted upon the first and second parts of the intervertebral implant.

In one embodiment, an intervertebral implant desirably includes a first implant part with a first magnetic element having a magnetically charged surface, and a first buoyant element coupled with the first magnetic element, and a second implant part opposing the first implant part, the second implant part including a second magnetic element having a second magnetically charged surface that opposes the first magnetically charged surface of the first magnetic element, and a second buoyant element coupled with the second magnetic element. The first and second magnetically charged surfaces preferably have the same polarity and are adapted to repel one another. The intervertebral implant preferably includes a fluid disposed between the first and second implant parts, whereby the first and second implant parts are moveable relative to one another and are in fluid communication with one another via the fluid.

In one embodiment, at least one of the first and second implant parts comprises a solid body having at least one aperture extending therethrough adapted for enabling the fluid to pass through the at least one aperture. The at least one aperture may include a plurality of apertures.

In one embodiment, the first and second parts of the intervertebral implant are moveable relative to one another. The first and second parts are preferably aligned with one another along an axis and are moveable relative to one another along the axis. In one embodiment, the first and second parts are adapted to move toward one another for compressing the fluid therebetween.

In one embodiment, the intervertebral implant preferably includes a first anchoring element coupled with the first part for anchoring the first part to the first vertebrae, and a second anchoring element coupled with the second part for anchoring the second part to the second vertebrae.

In one embodiment, an intervertebral implant desirably has a first part including a first magnetic element having a magnetically charged surface and a first buoyant element coupled with the first magnetic element, and a second part including a second magnetic element having a second magnetically charged surface that opposes the first magnetically charged surface of the first magnetic element and a second buoyant element coupled with the second magnetic element. The implant preferably includes a fluid disposed between the first and second parts, whereby the first and second parts are in fluid communication with the fluid and are adapted to move relative to one another. The intervertebral implant desirably includes an enclosure extending between the first and second parts for containing the fluid. The enclosure is desirably flexible for changing shape as the first and second parts move relative to one another.

In one embodiment, the flexible enclosure of the intervertebral implant is adapted to leech a medical solution such as a medicated fluid, liquid, or gel into the area of the spine surrounding the implant. In certain preferred embodiments, the fluid, liquid or gel may be a medicated solution including but not limited to analgesics, anti-inflammatories, steroids, antibiotics, etc. The flexible enclosure preferably functions as a reservoir for the medicated fluid, liquid or gel. The reservoir may be re-filled just as pain pumps are re-filled today.

After most disk replacement surgeries, a massive amount of pain medication is used, however, patients that receive the medicated intervertebral implant disclosed herein will be pain free. In one embodiment, when increased compression of the intervertebral implant occurs, more medication would be leeched out to inflammatory sites decreasing degeneration in the surrounding area. In one embodiment, the intervertebral implant has a microscopic two way opening that allows the medication to leech out and the device to be re-filled. In one embodiment, the implant has a first fluid chamber that does not leech so that the level of fluid therein remains constant and a second fluid chamber that leeches medication. The second fluid chamber that leeches medication is preferably re-fillable.

These and other preferred embodiments of the present invention will be described in more detail below.

BRIEF DESCRIPTION OF THE DRAWING

FIGS. 3A and 3B show an artificial knee implant including a hydromagnetic joint, in accordance with one embodiment of the present invention.

FIG. 4 shows a schematic of the medical implant and hydromagnetic joint of FIG. 2.

FIG. 8 shows a balance board including a hydromagnetic joint, in accordance with another embodiment of the present invention.

FIGS. 12A and 12B show a power generation system including a generator positioned atop hydromagnetic joints, in accordance with one embodiment of the present invention.

DETAILED DESCRIPTION

Figure 1:
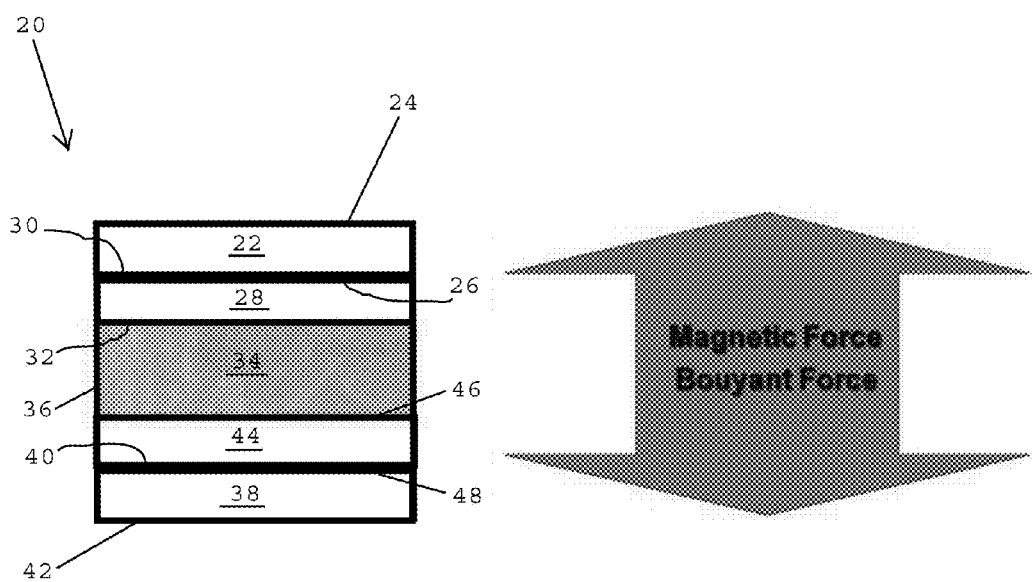
FIG. 1 shows a system including a hydromagnetic joint for dampening compression, tension and vibrational forces, in accordance with one embodiment of the present invention.

Referring to FIG. 1, in one embodiment, a hydromagnetic joint 20 includes a first buoyant element 22 having a top surface 24 and a bottom surface 26. The first buoyant element 22 is preferably buoyant in a liquid such as water. The hydromagnetic joint 20 also preferably includes a first magnetic element 28 having a negatively charged surface 30, and a positively charged surface 32.

The hydromagnetic joint 20 also desirably includes a body of a liquid 34, such as water, saline solution, or gel, bounded by a flexible enclosure 36, such as a flexible diaphragm, that enables the liquid body 34 to change shape in response to compression, tension, and vibrational forces applied to the hydromagnetic joint. The flexibility of the diaphragm may be varied in response to operational needs. In one embodiment, the hydromagnetic joint preferably includes a compressible fluid such as a compressible gas or a compressible liquid. In one embodiment, the compressibility of the fluid or liquid may be varied.

The hydromagnetic joint 20 also desirably includes a second buoyant element 38 having a top surface 40 and a bottom surface 42. The second buoyant element desirably has properties that are similar to the first buoyant element 22 so that it is adapted to float atop a liquid, such as water. The hydromagnetic joint 20 also desirably includes a second magnetic element 44 having a positively charged top surface 46, and a negatively charged bottom surface 48. The first and second magnetic elements 28, 44 are preferably made of ferromagnetic, diamagnetic, electromagnetic, or other well-known magnetic materials.

In the embodiment shown in FIG. 1, the positively charged surfaces of the first and second magnetic elements 28, 44 face one another. In other embodiments, however, the orientation of the first and second magnetic elements may be changed so that the opposing faces are negatively charged surfaces. The principal of operation remains consistent so long as the opposing faces of the first and second magnetic elements have common polarities so that they repel one another. The repelling force preferably increases as the opposing magnetically charged surfaces move closer to one another.

Although the present invention is not limited by any particular theory of operation, it is believed that the hydromagnetic joint 20 shown in FIG. 1 utilizes magnetism, buoyancy, and hydraulics to provide a nearly frictionless joint capable of preserving both mobility as well as minimizing energy losses. The first and second magnetic elements provide a repelling magnetic force as the magnetic elements are compressed toward one another. The first and second buoyant elements also provide a dampening force in response to compression of the buoyant elements toward one another. The hydromagnetic joint 20 exhibits gradual resistance to compression in a manner that cannot be achieved with conventional mechanical implants. The level of resistances may increase as the joint is further compressed. Moreover, the potential for structural breakdown of the joint elements is greatly minimized or reduced.

When the first and second buoyant elements 22, 38 are compressed toward one another, the interaction of the buoyant elements 22, 38 with the liquid body 34 generates a dampening or repelling force that opposes the compression forces. In addition, the opposing magnetic elements 28, 44 that are coupled with the respective first and second buoyant elements 22, 38 also provide a repelling force as shown by the large arrow in FIG. 1. Moreover, an electric field generated by the moving magnetic elements 28, 44 may yield additional energy that can be harnessed and utilized.

Figure 2:
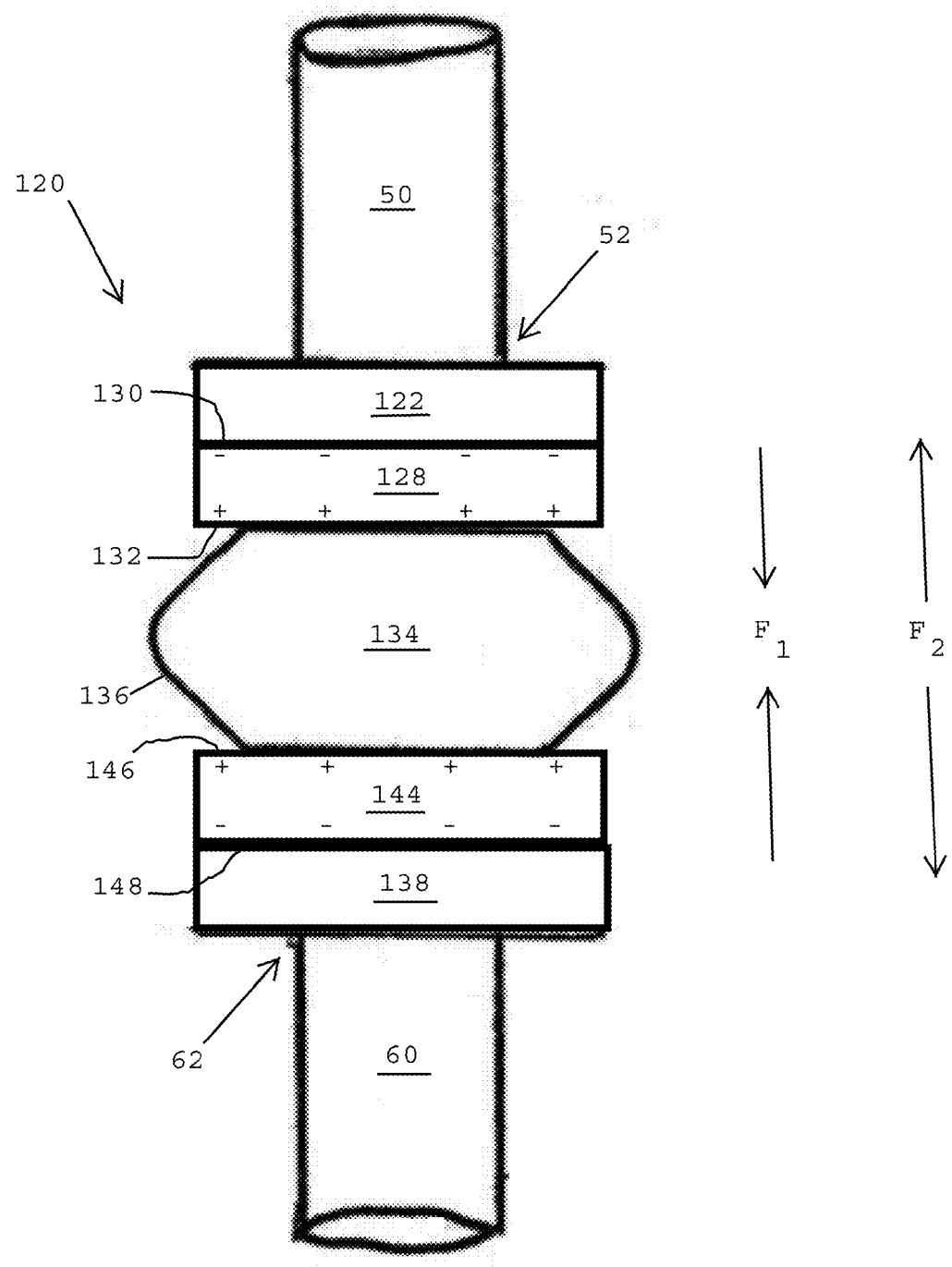
FIG. 2 shows a medical implant including a hydromagnetic joint, in accordance with one embodiment of the present invention.

Referring to FIG. 2, in one embodiment, a hydromagnetic joint 120 may be incorporated into a medical device such as an artificial knee. In one embodiment, a femur bone 50 has a lower end 52 and a tibia bone 60 has an upper end 62. The artificial knee including the hydromagnetic joint 120 preferably includes a first buoyant element 122, and a first magnetic element 128 coupled with the first buoyant element 122. The first magnetic element has a negatively charged face 130 and a positively charged face 132. The first buoyant element 122 and the first magnetic element 128 are preferably coupled together for moving simultaneously with one another. The hydromagnetic joint 120 desirably includes a liquid body 134, such as a body of water, contained within a flexible enclosure 136 for enabling movement of the liquid body in response to compression, tension, and vibrational forces.

The artificial knee with the hydromagnetic joint 120 also desirably includes a second buoyant element 138 coupled with the upper end 62 of the tibia 60, and a second magnetic element 144 coupled with the second buoyant element. The second magnetic element 144 includes a negatively charged face 148 and a positively charged face 146. The positively charged face 132 of the first magnetic element 128 desirably opposes the positively charged face 146 of the second magnetic element 144 to provide a magnetic repelling force between the first and second magnetic elements 128, 144. In other embodiments, however, the opposing surfaces of the first and second magnetic elements 128, 144 may be negatively charged for repelling one another.

In one embodiment, the femur 50 and the tibia 60 compress the hydromagnetic joint 120 therebetween so that a compressing force $F_1$ is applied to the liquid body 134. In response, the first and second buoyant element 122, 138 provide a repelling and/or dampening force that resists compression and the opposing positively charged faces of the first and second magnetic elements 128, 144 provide a repelling magnetic force. The combination of the repelling magnetic and buoyant forces is designated $F_2$.

FIG. 3A shows a human leg including the femur 50 and the tibia 60. A natural knee joint 70 is located between a lower end 52 of the femur 50 and an upper end 62 of the tibia 60. FIG. 3B shows the leg of FIG. 3A after the artificial knee including the hydromagnetic joint 120 of FIG. 2 has been implanted between the lower end 52 of the femur 50 and the upper end 62 of the tibia 60.

FIG. 4 shows a schematic view of the artificial knee implant including a hydromagnetic joint 120 positioned between the femur bone 50 and the tibia bone 60. The hydromagnetic joint 120 is represented in FIG. 4 as a box having an X positioned therein. The schematic showing a hydromagnetic joint 120 as a box with the X positioned therein is done to enhance clarity as to where the hydromagnetic joint is positioned in other embodiments disclosed herein.

Figure 5A:
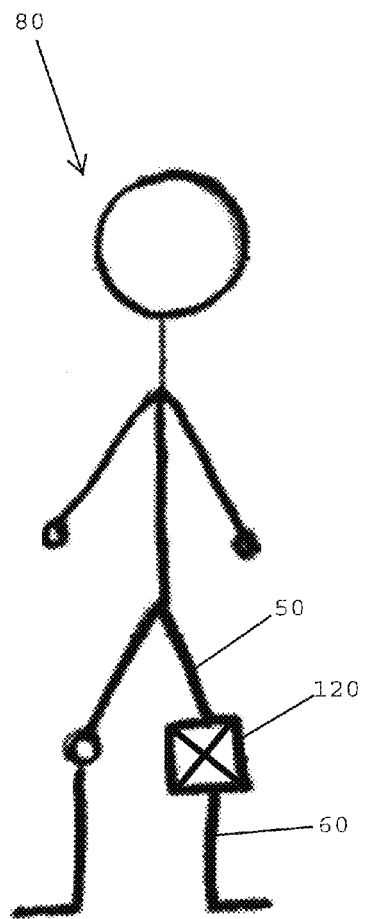
FIGS. 5A and 5B show an artificial knee implant including the hydromagnetic joint of FIG. 3B implanted in a patient.

Referring to FIG. 5A, in one embodiment, a patient 80 has a leg including a femur 50 and a tibia 60. An artificial knee including a hydromagnetic joint 120 is implanted between the lower end of the femur 50 and the upper end of the tibia 60 to provide a flexible hydromagnetic joint. The hydromagnetic joint is preferably flexible during movement of the patient's leg and dampens compression, tension and vibrational forces.

Figure 5B:
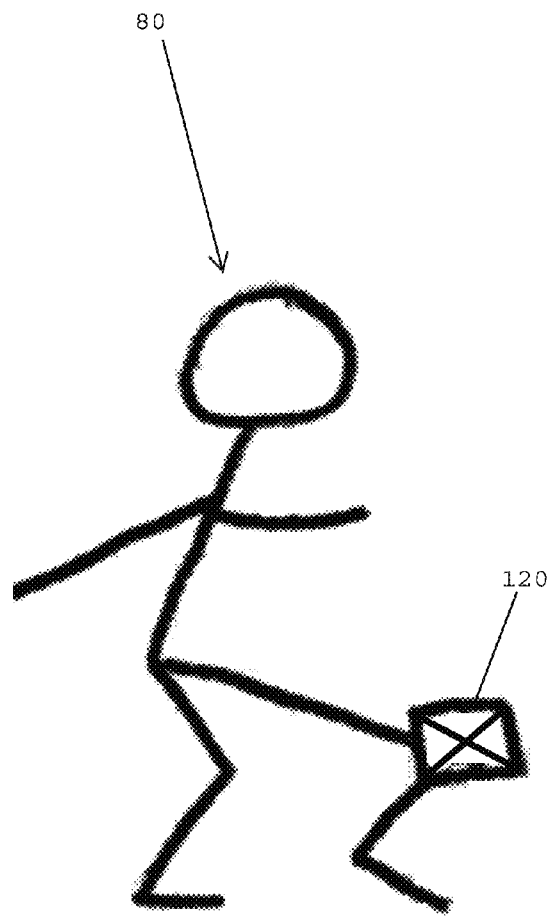

FIG. 5B shows an artificial knee with the hydromagnetic joint 120 during movement of the patient 80. The hydromagnetic joint 120 is adapted to accommodate flexing of the knee area of the patient and responds to compressive forces with opposing dampening and/or repelling forces created by the opposing buoyant elements and the opposing magnetic elements.

Figure 6:
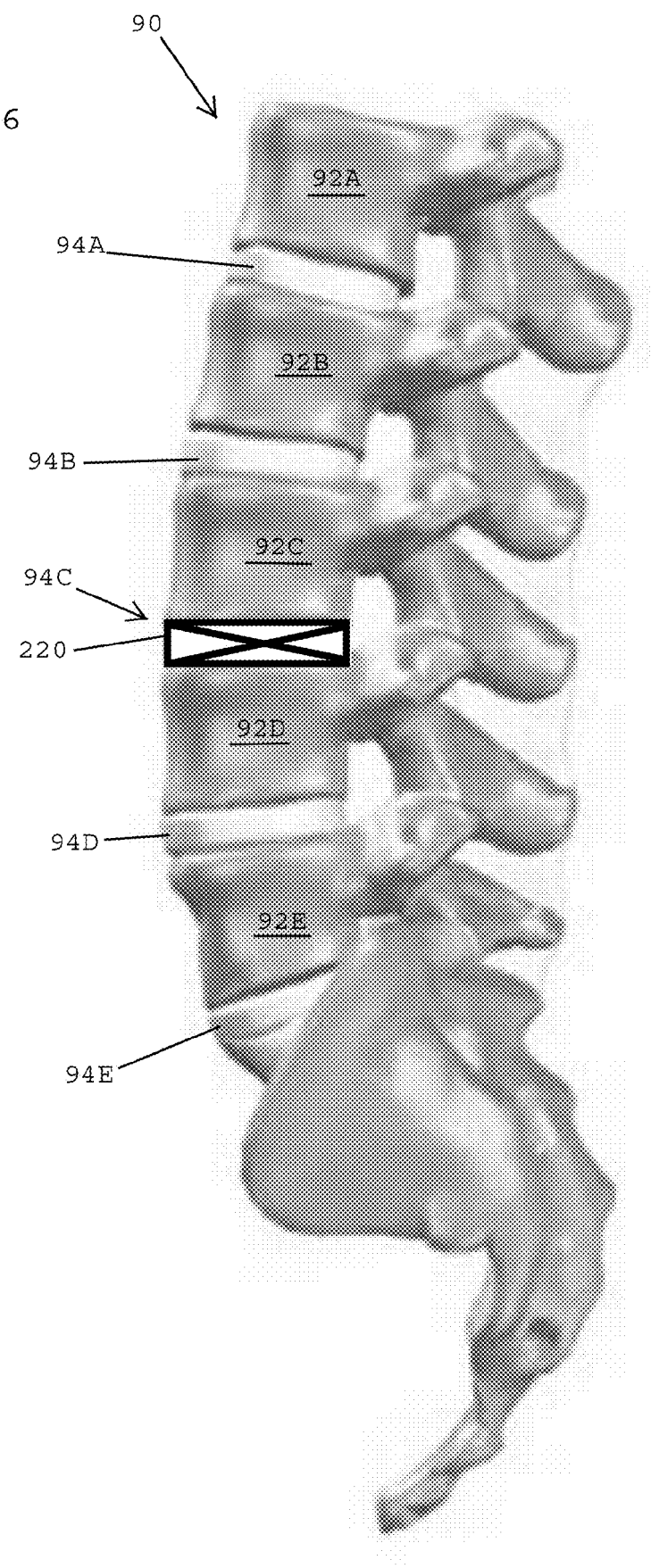
FIG. 6 shows an artificial intervertebral disc having a hydromagnetic joint, in accordance with one embodiment of the present invention.

Referring to FIG. 6, in one embodiment, a hydromagnetic joint may be incorporated into an intervertebral disc implant that is positioned within a disc space of a vertebral column. In FIG. 6, the vertebral column 90 includes vertebra 92A-92E having intervertebral discs 94A-94E therebetween. After disc 94C has been removed, an implant having a hydromagnetic joint 220 such as that shown and described herein may be positioned within the disc space between vertebra 92C and 92D. The hydromagnetic joint 220 of the implant provides flexibility between the adjacent vertebra 92C, 92D, while counteracting compressing forces due to the repelling forces generated by the hydraulic forces generated by the buoyant elements and magnetic elements of the joint 220.

Figure 7A:
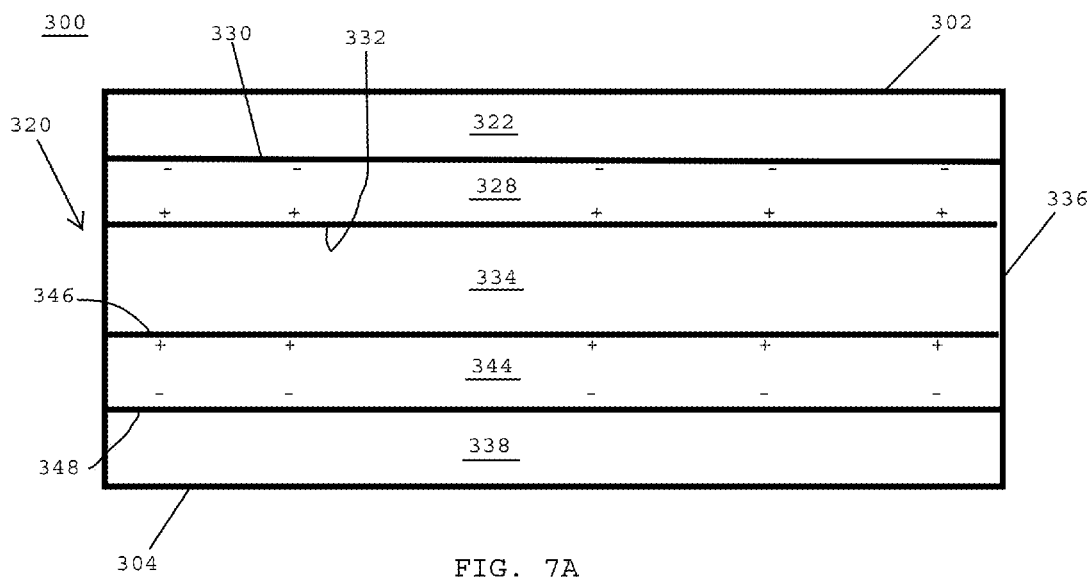
FIG. 7A shows a balance board including a hydromagnetic joint, in accordance with one embodiment of the present invention.

In one embodiment, the hydromagnetic joint disclosed herein may be incorporated into a balance board used for balancing therapy. Referring to FIG. 7A, in one embodiment, a balance board 300 includes a top surface 302 and a bottom surface 304 with a hydromagnetic joint 320 positioned between the respective top and bottom surfaces 302, 304. The hydromagnetic joint includes a first buoyant element 322 including the top surface 302 and a first magnetic element 328 coupled with the first buoyant element 322. The first magnetic element 328 includes a negatively charged surface 330 and a positively charged surface 332. The hydromagnetic joint also desirably includes a second buoyant body 338 that is coupled with a second magnetic element 344 having a positively charged surface 346 and a negatively charged surface 348. The hydromagnetic joint 320 desirably includes a liquid body 334 that is contained between the first and second buoyant bodies 322, 338.

Figure 7B:
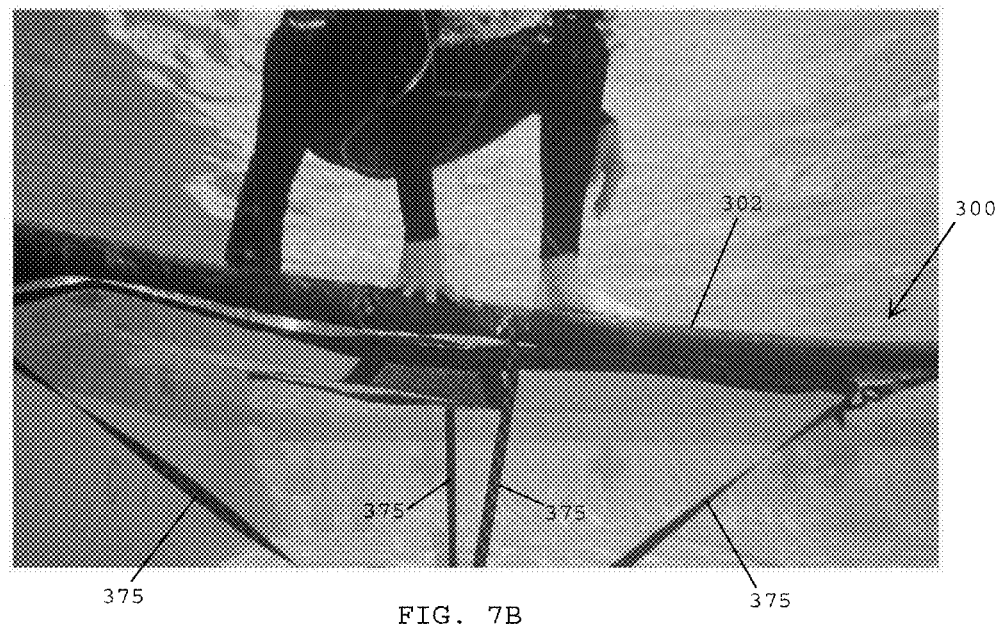
FIG. 7B shows a patient positioned atop the balance board of FIG. 7A for balancing therapy, in accordance with one embodiment of the present invention.

FIG. 7B shows a balance board 300 having the hydromagnetic joint 320 shown in FIG. 7A. An individual, such an amputee undergoing balancing therapy, may stand on the top surface 302 of the balance board 300. The balance board 300 is preferably immersed in an external body of water and held below the waterline via straps 375 that limit horizontal and vertical movement of the balance board 300 within the external body of water.

Referring to FIG. 8, in one embodiment, a patient 480 may use a balance board 400 for therapy. For example, a patient 480, having one or more limbs amputated, uses the board for balancing therapy to enhance balancing capabilities and prepare the patient for receiving prosthetic limbs. In FIG. 8, the balance board 400 includes a first buoyant element 422, a first magnetic element 428, a second buoyant element 438 and a second magnetic element 444. A liquid body 434 is disposed between the first and second magnetic elements 428, 444. In one embodiment, a flexible membrane 436 holds the liquid body 434 between the first and second magnetic elements 428, 444 and enables movement of the liquid body in response to compression and tension forces. The first magnetic element 428 has a first positively charged surface 432 and the second magnetic element 444 has a second positively charged surface 446 that opposes the first positively charged surface. In one embodiment, the patient 480 may wear boots 495 that have magnets incorporated therein that are magnetically attracted to the first magnetic element 428 for at least partially holding the patient 480 atop the balance board 400. The balance board 400 is desirably immersed in an external body of water 496. The balance board 400 is buoyant in the external body of water 496 so that the patient 480 may balance on a top surface 402 of the balance board 400 for participating in balancing therapy.

Thousands of U.S. Service members have been wounded in Iraq. These combat survivors often sustain multiple traumas and develop physical and mental injuries. The term polytrauma refers to concurrent injury to the brain and several body areas or organ systems that result in physical, cognitive, and psychosocial impairments. While many therapeutic modalities are available for patients with polytrauma, only a few modalities simultaneously address global rehabilitation, including pain, vestibular impairment, and cognitive symptoms. The sport of surfing involves aspects of hydrotherapy, strength training, balance rehabilitation, and group supportive therapy.

Surfing therapy may be used to help patients improve their proficiency in walking, balancing, and vestibular functions, as well as gain muscular strength, aerobic endurance, concentration, and timing of wave movements. The devices shown in FIGS. 7A-7B and 8 of the present application may be used as part of a surfing therapy protocol as part of a multi-modal treatment for patients with polytrauma.

Surfing therapy provides patients, such as amputees, with an environment and means by which to engage in physical activities they enjoy and which challenge them physically, mentally, and emotionally. It preferably includes vestibular instruction, water safety, swimming, paddling, and wave riding and focuses on the physical and psychological skills needed for these activities, including balance, muscular strength, aerobic endurance, as well as skills in concentration and timing of wave movement. Discussions among veteran mentors, who are also wounded warriors, local lifeguards, and new program participants may also take place while participating in surfing therapy.

Although the present invention is not limited by any particular theory of operation, it is believed that there are several potential mechanisms by which surfing may help patients. Pain management is most likely established through endogenous opioid pathways that increase with exercise. It is unclear why patients may report greater improvements in pain with surfing than with other forms of exercise; it may, however, go along with theories of long-term potentiation. The patients enjoy—and are excited by—their time surfing. Pleasurable experiences are associated with increases in norepinephrine and serotonin, and these pathways may, in turn, feedback on long-term potentiating and pain.

The most encouraging aspect of surfing as therapy may be its impact on vestibular function. Traditional vestibular rehabilitation involves the use of a balance platform. While this platform may be helpful, many patients feel they "max the machine" early on. In other words, the rehabilitation challenges are not as strenuous as are the tasks that a patient may face in the real world. Surfing allows additional progress. The task of surfing is similar to that encountered on a traditional balance board, with the additional feature of movement. This may more closely approximate the problem of walking with a prosthetic, and other complicated vestibular issues. New developments will be required to recreate the vestibular challenge of walking without the ocean. Patients may be able to show greater, real-world progress after mastering the art of surfing.

It is also believed that surfing therapy may improve psychological symptoms. This may be because surfing combines two modalities often used today to assist in psychiatric illness: components of group therapy and exercise. In one embodiment, trauma survivors may congregate on shore to learn the mechanics of surfing and also to communicate with each other while they wait to catch the next wave. Interspersed with the waiting and talking are the strenuous exercise and excitement of actually catching a wave. Large muscular movements can increase the body's serotonin norepinephrine and dopamine neurotransmitters. Excitement is also independently associated with increases in both of these neurotransmitters. These neurotransmitter systems are commonly decreased in PTSD and depression, and it is possible that surfing helps normalize these systems.

Surfing therapy has great potential for multi-modal treatment for patients with polytrauma. Additional research and development is needed to see if the therapeutic benefit, including vestibular/balance enhancement, pain resolution, and behavioral improvement, is attributable to participating in surfing therapy. In addition, for those patients not located near the ocean, additional research is required to determine if new balancing devices (e.g. the embodiments shown in FIGS. 7A-7B and 8) and new prosthetics may be used to translate the surfing experience and benefits to a therapy pool at rehabilitation centers not located near the ocean.

Figure 9:
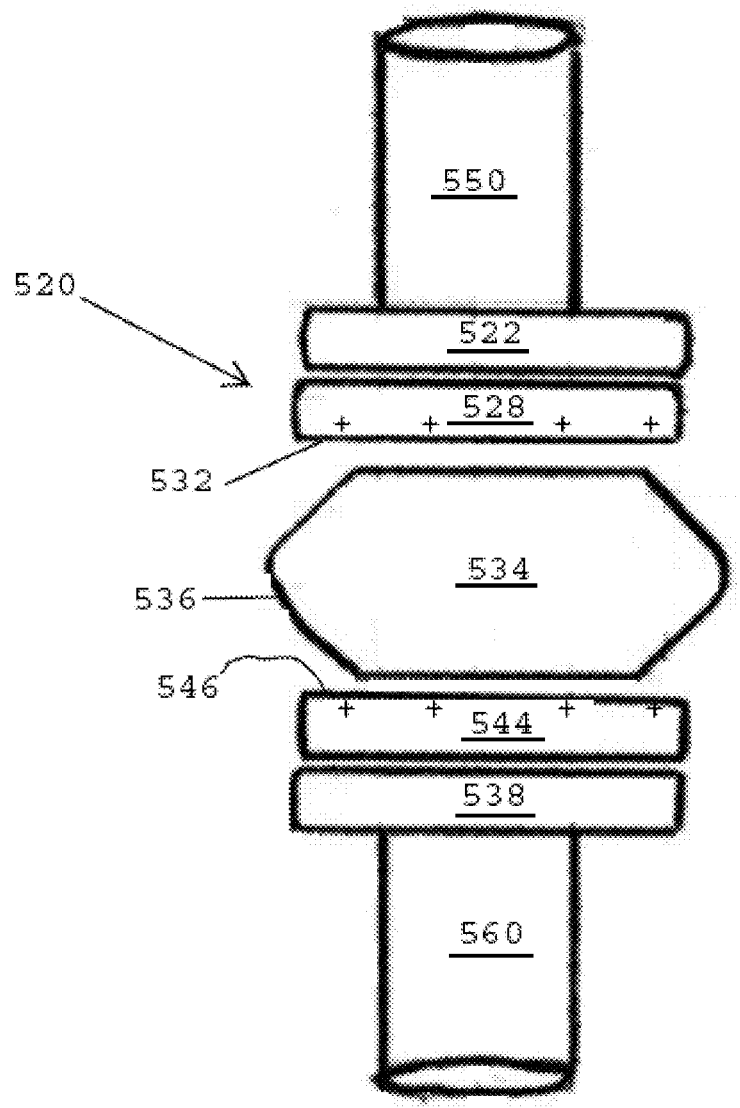
FIG. 9 shows a spring including a hydromagnetic joint, in accordance with one embodiment of the present invention.

Referring to FIG. 9, in one embodiment, a hydromagnetic joint 520 may be utilized as a spring. In one embodiment, the hydromagnetic joint 520 is desirably positioned between a first shaft 550 and a second shaft 560 of a mechanical system. The hydromagnetic joint 520 includes a first buoyant element 522 attached to the first shaft 550, a first magnetic element 528 coupled with the first buoyant element, a liquid body 534, a second magnetic element 544 and second buoyant element 538 attached to the second shaft 560. The first magnetic element 528 is desirably coupled with the first buoyant element 522. The liquid body 534 is preferably positioned between the first and second magnetic elements 528, 544 and bounded by a flexible diaphragm 536. The second magnetic element 544 is preferably coupled with the first buoyant element 538, which, in turn, is connected with the second shaft 560. The first and second magnetic elements 528, 544 have opposing positively charged surfaces 532, 546. In operation, as the first and second shafts 550, 560 move toward one another for compressing the hydromagnetic joint 520 therebetween, the magnetic elements 528, 544 repel one another and the buoyant elements 522, 538 use hydraulic forces to dampen compression via the liquid body 534.

Figure 10:
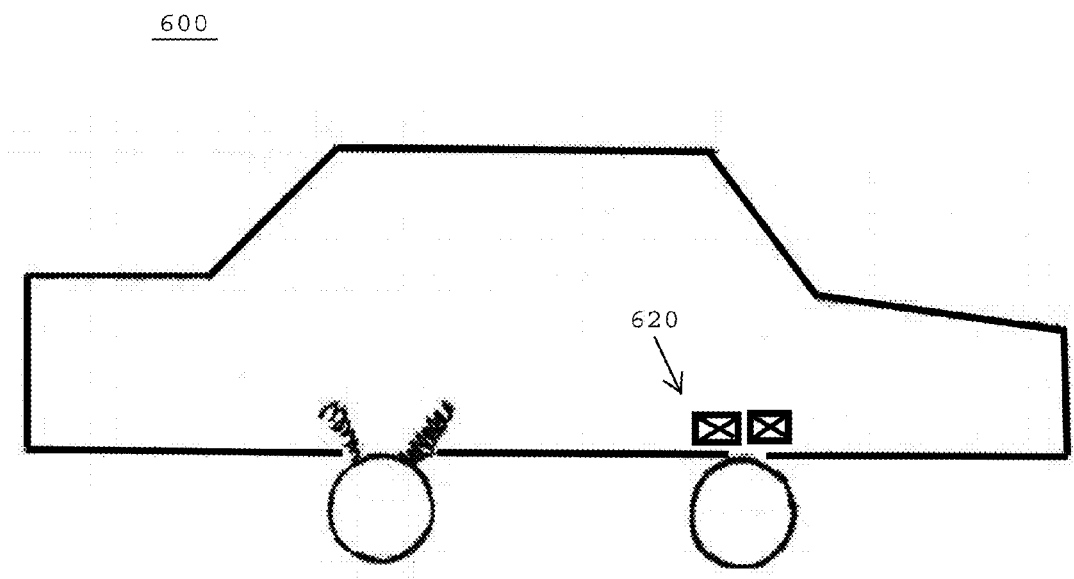
FIG. 10 shows a vehicle including a shock absorbing system having one or more hydromagnetic joints, in accordance with one embodiment of the present invention.

Referring to FIG. 10, in one embodiment, a vehicle 600, such as a truck or car, may include one or more hydromagnetic joints 620 that are used in lieu of, or incorporated into, springs or shock absorbers for providing a dampening force during operation of the vehicle 600.

Figure 11:
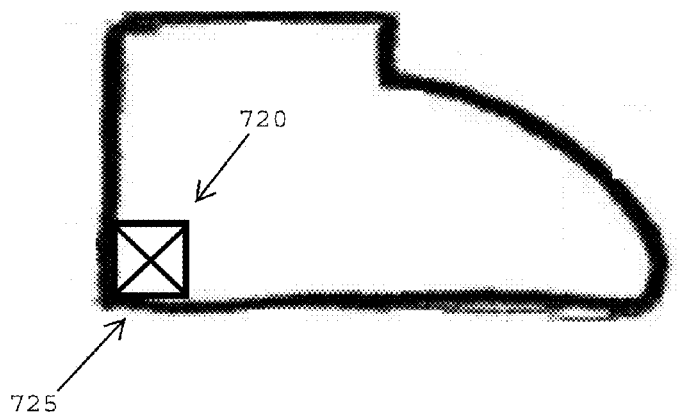
FIG. 11 shows a shoe including a heel having a hydromagnetic joint, in accordance with one embodiment of the present invention.

Referring to FIG. 11, in one embodiment, a shoe or sneaker 700 may have a hydromagnetic joint 720 incorporated therein for providing cushioning and/or dampening forces. In one embodiment, the hydromagnetic joint 720 is incorporated into the heel region 725 of a shoe or sneaker for counteracting compression forces on the heel.

Referring to FIGS. 12A and 12B, in one embodiment, a power generation system includes a generator 800 such as a gas or diesel powered generator. The generator vibrates during operation, which may cause excessive noise and energy loss. In one embodiment, a plurality of hydromagnetic joints 820 may be positioned to support the generator for counteracting the vibrational forces created during operation of the generator. The hydromagnetic joints desirably minimize and/or eliminate vibration of the generator 800, which minimizes noise, and saves heat energy losses due to less vibration of the generator 800. As such, the hydromagnetic joints 820 will provide for more efficient and quieter operation of a generator. In one embodiment, additional hydromagnetic joints may be positioned beneath the generator 800 for minimizing vibration.

Figure 13:
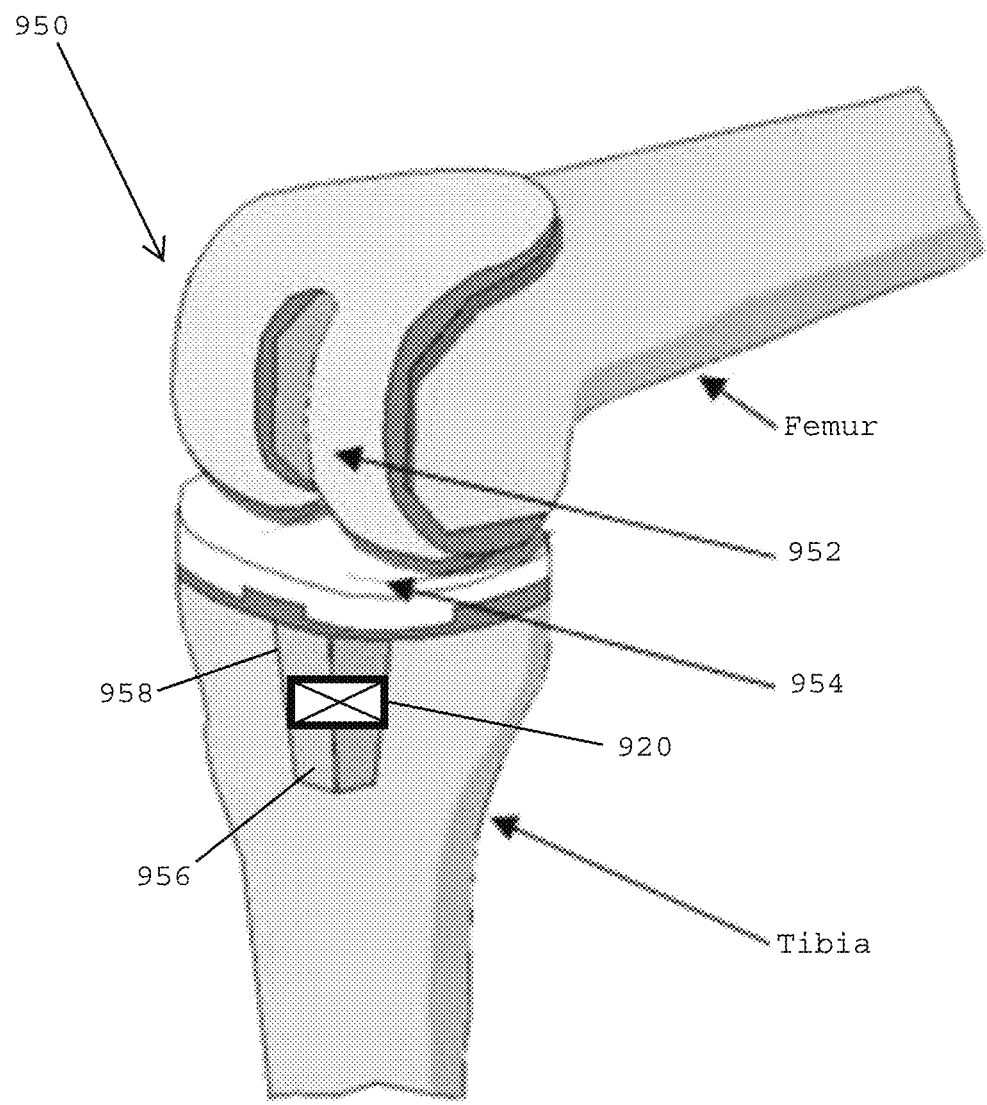
FIG. 13 shows an artificial knee including a hydromagnetic joint disposed in a bone anchoring element, in accordance with one embodiment of the present invention.

Referring to FIG. 13, in one embodiment, a hydromagnetic joint 920 may be incorporated into a medical device such as an artificial knee 950. The artificial knee 950 desirably includes a first implant part 952 secured to a lower end of a femur and a second implant part 954 secured to an upper end of a tibia. The second implant part 954 desirably includes an anchoring post 956 that is inserted into a bore 958 formed at the upper end of the tibia. The anchoring post 956 desirably has a hydromagnetic joint 920 disposed therein for absorbing compression and tension forces exerted upon the artificial knee 950. In other embodiments, the hydromagnetic joint 920 may be disposed within an anchoring post associated with the first implant part 952. Although FIG. 13 shows a hydromagnetic joint integrated into an artificial knee, one or more hydromagnetic joints may be integrated into other medical devices such as a hip replacement device or a spinal implant.

Figure 14:
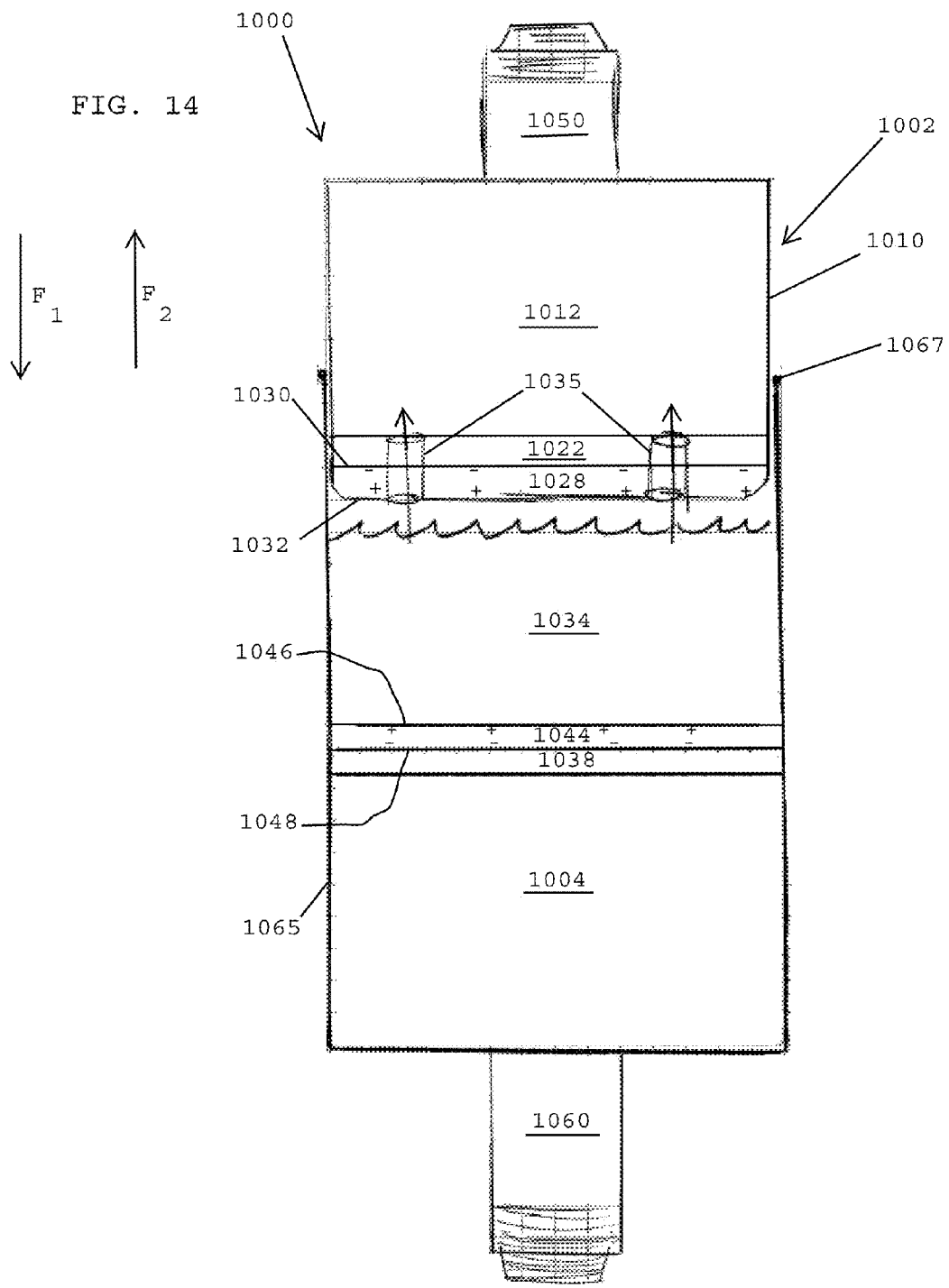
FIG. 14 shows a hydromagnetic joint having apertures that control the compression rate of the joint, in accordance with another embodiment of the present invention.

Referring to FIG. 14, in one embodiment, a hydromagnetic joint 1000 preferably includes a mobile element 1002 and a stationary element 1004. The mobile element 1002 preferably includes an outer wall 1010 that defines an enclosed internal chamber 1012. The mobile element 1002 preferably includes a first shaft 1050 coupled with the mobile element 1002. The mobile element 1002 also desirably includes a first buoyant element 1022 and a first magnetic element 1028 coupled with the first buoyant element. The first magnetic element 1028 preferably has a negatively charged major face 1030 and a positively charged major face 1032. The mobile element 1002 also desirably includes one or more apertures 1035 that extend through the first buoyant element 1022 and the first magnetic element 1028. The size and the number of apertures 1035 may be modified to control the flow rate of a liquid through the apertures, which, in turn, controls the compression rate of the joint. The size of the apertures or the number of apertures that are open may be controlled by a control system, such as an electronic control system having one or more central processing units.

The stationary element 1004 preferably includes a second shaft 1060 and an outer wall 1065 that extends away from the second shaft to an opening 1067 located at an upper end of the outer wall 1065. The stationary element 1004 preferably includes a second buoyant element 1038 and a second magnetic element 1044 coupled with the second buoyant element. The second magnetic element 1044 includes a positively charged major surface 1046 and a negatively charged major surface 1048. The positively charged major surface 1046 of the second magnetic element 1044 preferably opposes the positively charged major surface 1032 of the first magnetic element 1028 so that the first and second magnetic elements repel one another. In one embodiment, the first and second magnetic elements may have negatively charged magnetic surfaces that oppose one another. A liquid 1034 preferably fills a space between the second magnetic element 1044 and the opening 1067 at the upper end of the outer wall 1065.

In operation, as the mobile element 1002 is compressed toward the stationary element 1004 by a compressing force $F_1$, the liquid 1034 passes through the apertures 1035 of the mobile part and fills the internal chamber 1012. As the mobile element 1002 continues to move toward the stationary element 1004, additional liquid 1034 passes through the apertures 1035 and fills the internal chamber 1012. As noted above, the size of the apertures 1035 will control the rate of the liquid flowing through the apertures. The size and/or number of apertures 1035 may be modified for controlling the rate of liquid passing therethrough, which, in turn, controls the compression rate of the hydromagnetic joint.

At a particular stage of compression, fluid completely fills the internal chamber 1012 of the mobile element for stopping further movement of the mobile part relative to the stationary element. At this stage, the liquid is not flexible, thereby stopping the mobile element 1002 before coming into contact with the stationary element 1004, leaving a small amount of liquid 1034 in between the mobile element and the stationary element at full compression.

In one embodiment, a hydromagnetic joint may be disposed within a tube, diaphragm, bag or outer casing so that magnets do not become misaligned and so that the diaphragm does not extend beyond a certain diameter when compressed.

In one embodiment, the closer a tube or outer casing is located to the hydromagnetic joint, the more the joint functions as a hydraulic piston.

In one embodiment, the enclosure for a hydromagnetic joint is flexible. In one embodiment, however, when the mobile element is fully compressed toward the stationary element, the flexible enclosure for the liquid is no longer flexible and the liquid between the mobile and stationary elements functions as a hydraulic stop for halting movement of the mobile element before it comes in contact with the stationary element.

At a particular stage of compression, the opposing positively charged faces of the first and second magnetic elements 1028 and 1044 repel one another to push the mobile part 1002 away from the stationary element 1004 by a force designated $F_2$. As the mobile element 1002 and the stationary element 1004 move away from one another, the liquid 1034 is drawn from the internal chamber 1012 and passes through the apertures 1035 for filling the central chamber of the stationary element 1004. The hydromagnetic joint shown in FIG. 14 may be incorporated into any of the embodiments disclosed in the present application including medical implant devices.

Figure 15:
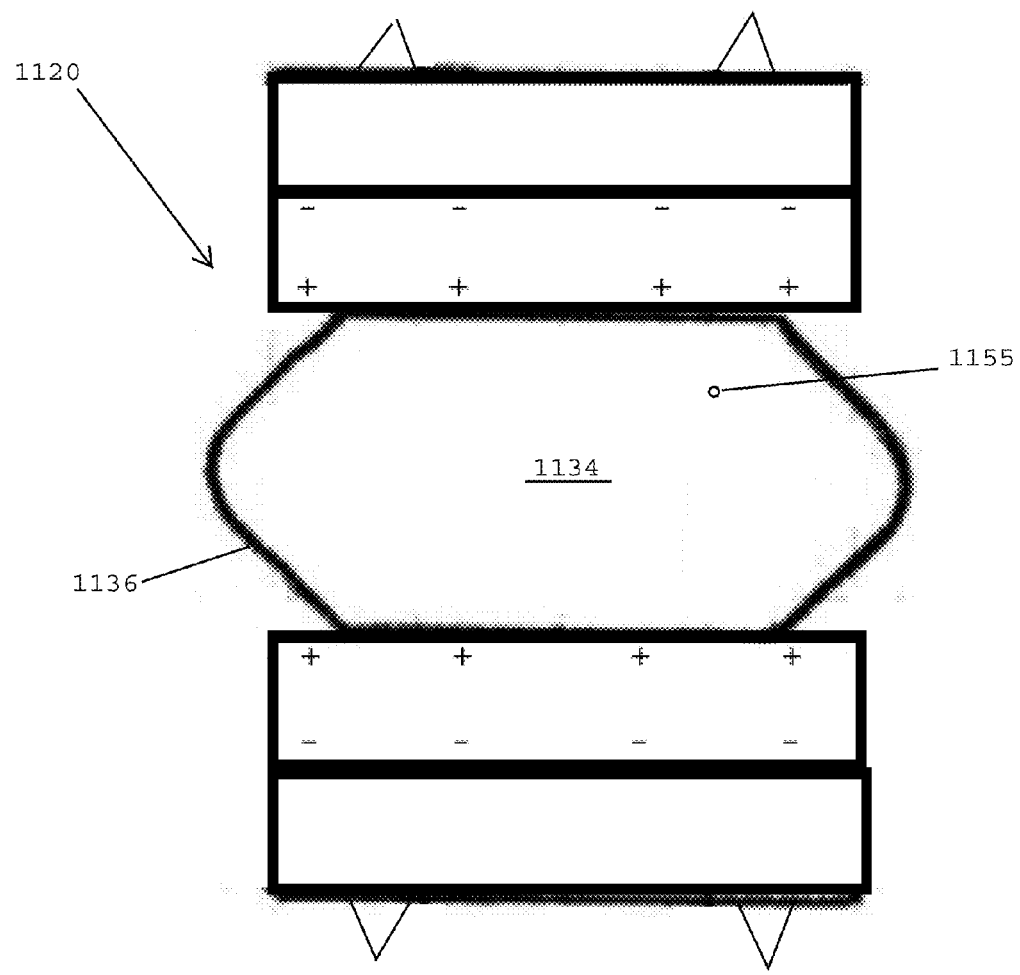
FIG. 15 shows an intervertebral disc having a hydromagnetic joint including a fluid reservoir adapted to leech a medicated solution, in accordance with one embodiment of the present invention.

When using conventional disk replacement devices, medication such as pain medication is typically used to provide pain relief. Referring to FIG. 15, in one embodiment of the present invention, an intervertebral implant 1120 includes an enclosure 1136 that is adapted to leech a medical solution 1134 such as a medicated fluid, liquid, or gel into the area of the spine surrounding the implant. In certain preferred embodiments, the fluid, liquid or gel may be a medicated solution including but not limited to analgesics, anti-inflammatories, steroids, antibiotics, etc. The flexible enclosure 1136 preferably functions as a reservoir for the medicated fluid, liquid or gel. The reservoir may be re-filled using one or more resealable openings 1155 that extend through the outer wall of the flexible enclosure 1136. In one embodiment, the enclosure 1136 is porous or includes one or more microscopic openings for allowing the medicated solution to slowly pass through the outer wall of the enclosure and into the surrounding tissue and bone. The enclosure may also include one or more fill ports for re-filling the enclosure with the medicated fluid, solution or gel.

In one embodiment, when increased compression of the intervertebral implant 1120 occurs, more medication would be leeched out from the enclosure 1136 to inflammatory sites decreasing degeneration in the surrounding area and increasing acceptance of the implant. In one embodiment, the intervertebral implant has a microscopic two way opening 1155 that allows the medication to leech out and the device to be re-filled.

Figure 16:
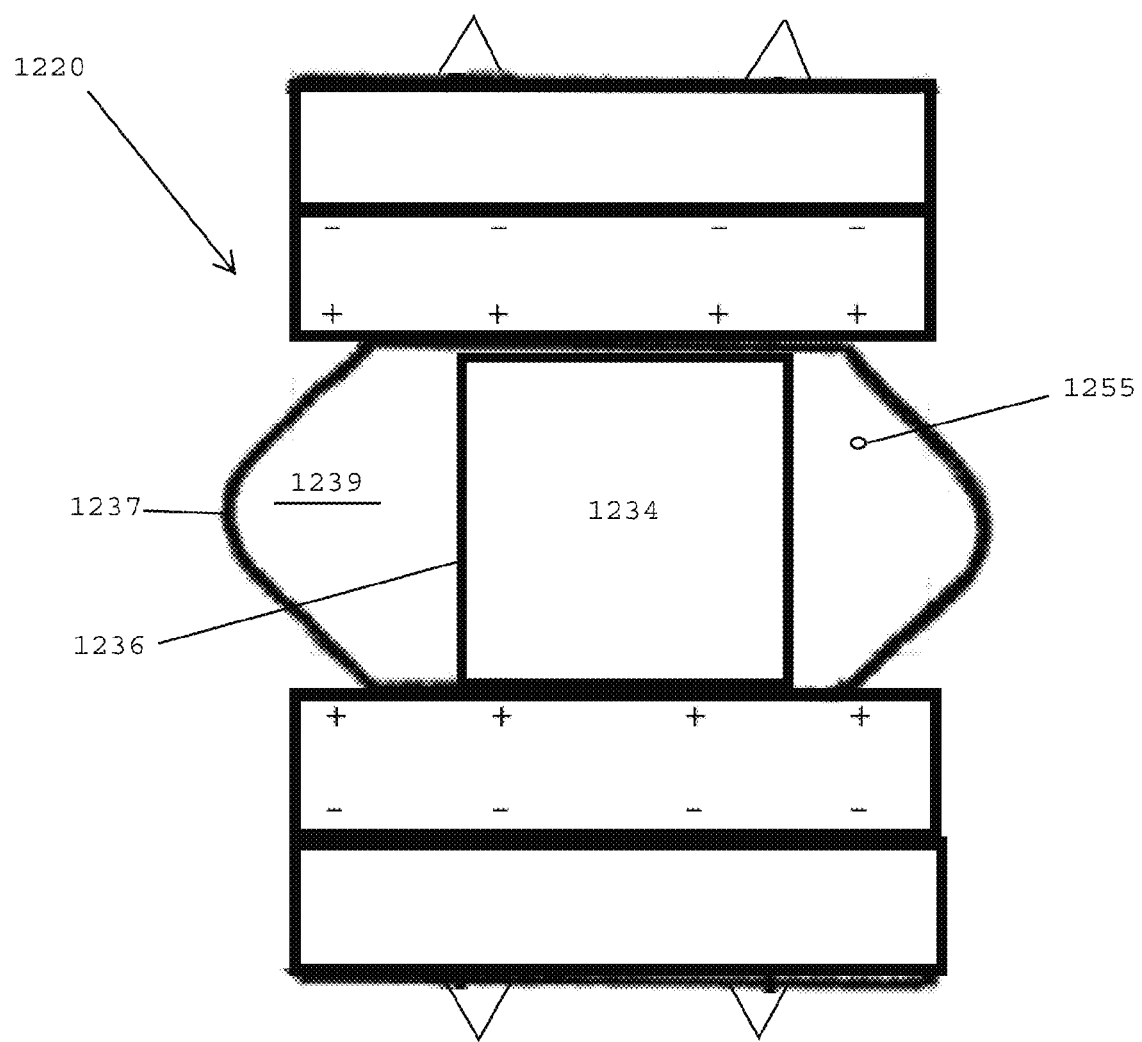
FIG. 16 shows an intervertebral disc having a hydromagnetic joint including a first reservoir for a fluid and a second reservoir adapted to leech a medicated solution.

Referring to FIG. 16, in one embodiment, an intervertebral disc implant 1220 has a first fluid chamber 1236 that contains a fluid 1234 that does not leech so that the volume of fluid therein remains constant therein. The implant 1220 preferably has a second fluid chamber 1237 adapted to leech a medicated solution 1239 after implantation. The second fluid chamber that leeches medication is preferably re-fillable via one or more resealable openings 1255. The openings for leeching may be positioned around the perimeter of the enclosure for providing the medicated solution completely around the implant.

In one embodiment, a system or medical device having a hydromagnetic joint preferably conserves vibrational energy by transferring dampening or repelling energy into at least some of the energy used for a patient's next step or a system's (e.g., a generator) next cycle. For example, when a medical implant having a hydromagnetic joint is compressed, the dampening and/or repelling magnetic forces may be harnessed for transferring energy into the patient's next step. Just as a runner can have a spring in his or her step when moving from touching his or her toes to standing upright, a medical implant having a hydromagnetic joint may provide a spring in its upward motion as it goes from a compressed state to an expanded state. The conserved energy may also be used for rotating a rotating generator.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A knee implant comprising:
    a first implant part adapted for attachment to a femur;
    a second implant part adapted for attachment to a tibia;
    said knee implant including a hydromagnetic joint comprising
        a first magnetic element having a first magnetically charged surface and a first buoyant element coupled with said first magnetic element,
        a second magnetic element having a second magnetically charged surface that opposes said first magnetically charged surface of said first magnetic element and a second buoyant element coupled with said second magnetic element,
        a fluid body disposed between said first and second buoyant elements, wherein said first and second buoyant element are in fluid communication with one another through said fluid body, and
        an enclosure extending between said first and second buoyant elements for containing said fluid body therebetween, wherein said first and second buoyant elements are moveable relative to one another.

2. The knee implant as claimed in claim 1, wherein said hydromagnetic joint is disposed between said first and second implant parts.

3. The knee implant as claimed in claim 1, wherein at least one of said first and second implant parts comprises an anchoring post.

4. The knee implant as claimed in claim 3, wherein said hydromagnetic joint is disposed within said anchoring post.

5. The knee implant as claimed in claim 4, wherein said first implant part includes said anchoring post.

6. The knee implant as claimed in claim 4, wherein said second implant part includes said anchoring post.

7. The knee implant as claimed in claim 1, wherein said first and second magnetically charged surfaces have a common polarity so that said first and second magnetically charged surfaces repel one another.

8. The knee implant as claimed in claim 1, wherein said fluid body comprises a liquid or a gel.

9. The knee implant as claimed in claim 8, wherein said liquid or gel is medicated and said enclosure comprises one or more openings adapted to leech said medicated liquid or gel into an area surrounding said intervertebral implant.

10. The knee implant as claimed in claim 1, wherein said enclosure is a flexible enclosure adapted to change shape as said first and second implant parts move relative to one another, and wherein said fluid body and said flexible enclosure are adapted to change shape in response to compression forces exerted upon said first and second implant parts.

11. A knee implant comprising:
a first implant part including a first magnetic element having a magnetically charged surface, and a first buoyant element coupled with said first magnetic element;
a second implant part opposing said first implant part, said second implant part including a second magnetic element having a second magnetically charged surface that opposes said first magnetically charged surface of said first magnetic element, and a second buoyant element coupled with said second magnetic element;
a fluid disposed between said first and second implant parts, wherein said first and second implant parts are moveable relative to one another and are in fluid communication with said fluid.

12. The knee implant as claimed in claim 11, wherein said fluid is contained within an enclosure that is disposed between said first and second implant parts.

13. The knee implant as claimed in claim 12, wherein said enclosure for said fluid is flexible, and wherein said fluid is medicated.

14. The knee implant as claimed in claim 11, wherein said first and second parts are moveable relative to one another.

15. The knee implant as claimed in claim 11, wherein said first and second parts are adapted to move toward one another for compressing said fluid therebetween.

16. The knee implant as claimed in claim 11, wherein said first and second magnetically charged surfaces have the same polarity and are adapted to repel one another.

17. The knee implant as claimed in claim 11, further comprising:
a first anchoring post coupled with said first implant part for anchoring said first implant part to a femur; and
a second anchoring post coupled with said second implant part for anchoring said second implant part to a tibia.

18. The knee implant as claimed in claim 17, wherein said first and second magnetic elements are disposed within said first anchoring post.

19. The knee implant as claimed in claim 17, wherein said first and second magnetic elements are disposed within said second anchoring post.

20. A knee implant comprising:
a first part including a first magnetic element having a magnetically charged surface and a first buoyant element coupled with said first magnetic element;
a second part including a second magnetic element having a second magnetically charged surface that opposes said first magnetically charged surface of said first magnetic element and a second buoyant element coupled with said second magnetic element; and
a fluid disposed between said first and second parts, wherein said first and second parts are in fluid communication with said fluid and are adapted to move relative to one another.

* * * * *